United States Patent [19]
Farley

[11] Patent Number: 4,989,587
[45] Date of Patent: Feb. 5, 1991

[54] STERNAL RETRACTOR

[76] Inventor: Daniel K. Farley, 601 E. Lake Shore Dr., Barrington, Ill. 60010

[21] Appl. No.: 343,784

[22] Filed: Apr. 26, 1989

[51] Int. Cl.[5] .............................................. A61B 17/02
[52] U.S. Cl. ................................................... 128/20
[58] Field of Search ...................... 128/20, 17; 269/328

[56] References Cited

U.S. PATENT DOCUMENTS

| | | | |
|---|---|---|---|
| 1,963,173 | 6/1934 | Morin | 128/20 |
| 2,053,868 | 9/1936 | Grosso | 128/20 |
| 3,040,739 | 6/1962 | Grieshaber | 128/20 |
| 3,168,093 | 2/1965 | Gauthier | 128/20 |
| 3,221,743 | 12/1965 | Thompson et al. | 128/20 |
| 3,522,799 | 8/1970 | Gauthier | 128/20 |
| 3,572,326 | 3/1971 | Jensen | 128/20 |
| 3,710,783 | 1/1973 | Jascalevich | 128/20 |
| 3,724,449 | 4/1973 | Gauthier | 128/20 |
| 3,965,890 | 6/1976 | Gauthier | 128/20 |
| 4,143,652 | 3/1979 | Meier et al. | 128/20 |
| 4,254,763 | 3/1981 | McCready et al. | 128/20 |
| 4,355,631 | 10/1982 | LeVahn | 128/20 |
| 4,424,724 | 1/1984 | Bookwalter et al. | 128/20 |
| 4,457,300 | 7/1984 | Budde | 128/20 |
| 4,461,284 | 7/1984 | Fackler | 128/20 |
| 4,467,791 | 8/1984 | Cabrera et al. | 128/20 |
| 4,510,926 | 4/1985 | Inaba | 128/20 |
| 4,617,916 | 10/1986 | LeVahn et al. | 128/20 |
| 4,702,230 | 10/1987 | Pelta | 128/20 |
| 4,726,356 | 2/1988 | Santilli et al. | 128/20 |
| 4,797,394 | 5/1988 | Watanabe | 128/20 |

OTHER PUBLICATIONS

Advertisement Catalog No. 8895-20 and 8898-2-0—Koros Surgical Instruments Corp.
Advertisement Catalog No. 8840-05—Koros Surgical Instruments Corp.
Advertisement Catalog No. 34-1150—Pilling.
Omni-Tract Flyer (undated).

Primary Examiner—Edward M. Coven
Assistant Examiner—Mark S. Graham
Attorney, Agent, or Firm—Held & Malloy, Ltd. McAndrews

[57] ABSTRACT

A sternal retraction apparatus for cardiac surgery and dissection of the Internal Mammary Artery (IMA) includes a support post fastened to a surgical table rail and an extension arm connected to the support post by an adjustable connection joint for holding the apparatus over the sternum of a patient. A pair of adjustable retraction arms is connected to the support post by means of a pivotal joint which enables the apparatus to separate the sternum as well as elevate the rib cage for sternal exposure. Retractor blades connected directly to the retraction arms extend downwardly through an incision to retract the sternum.

14 Claims, 5 Drawing Sheets

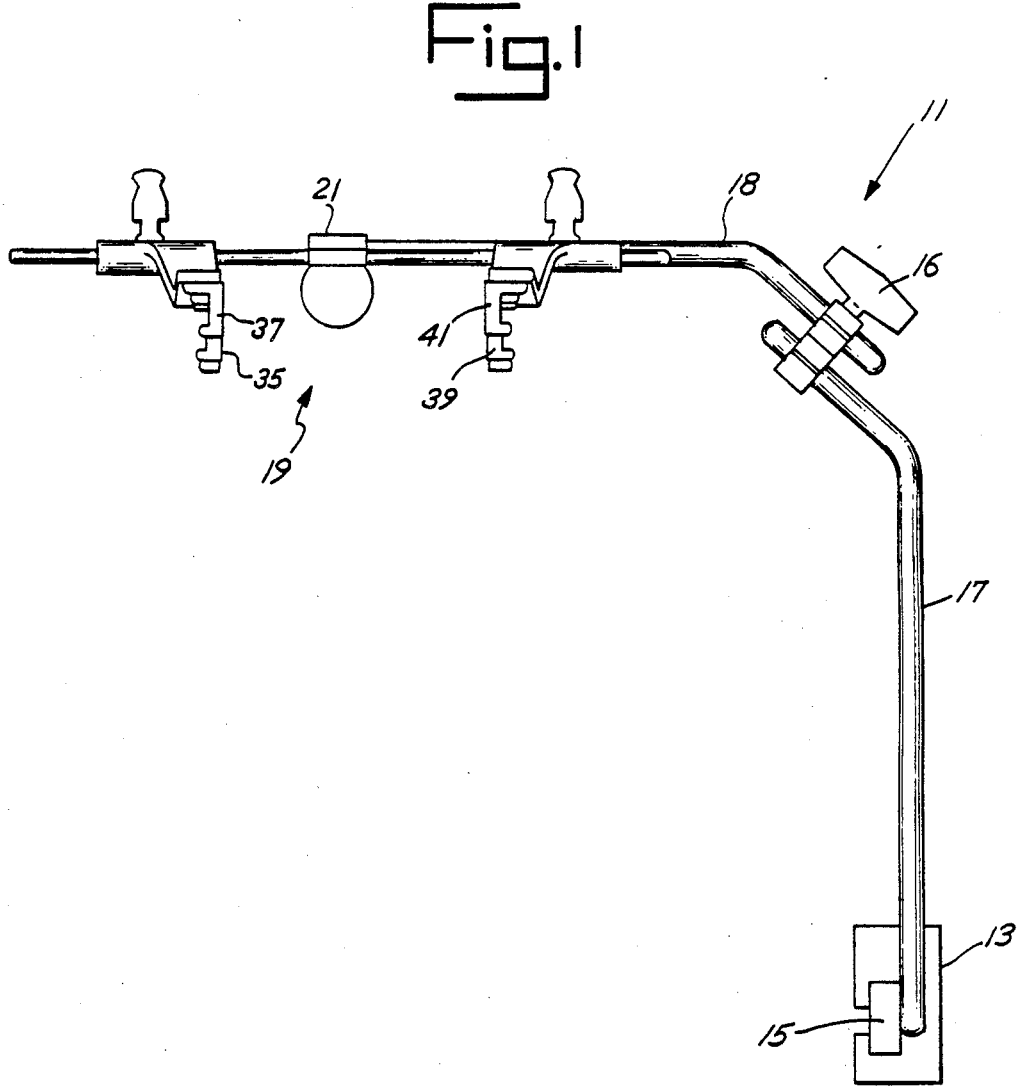

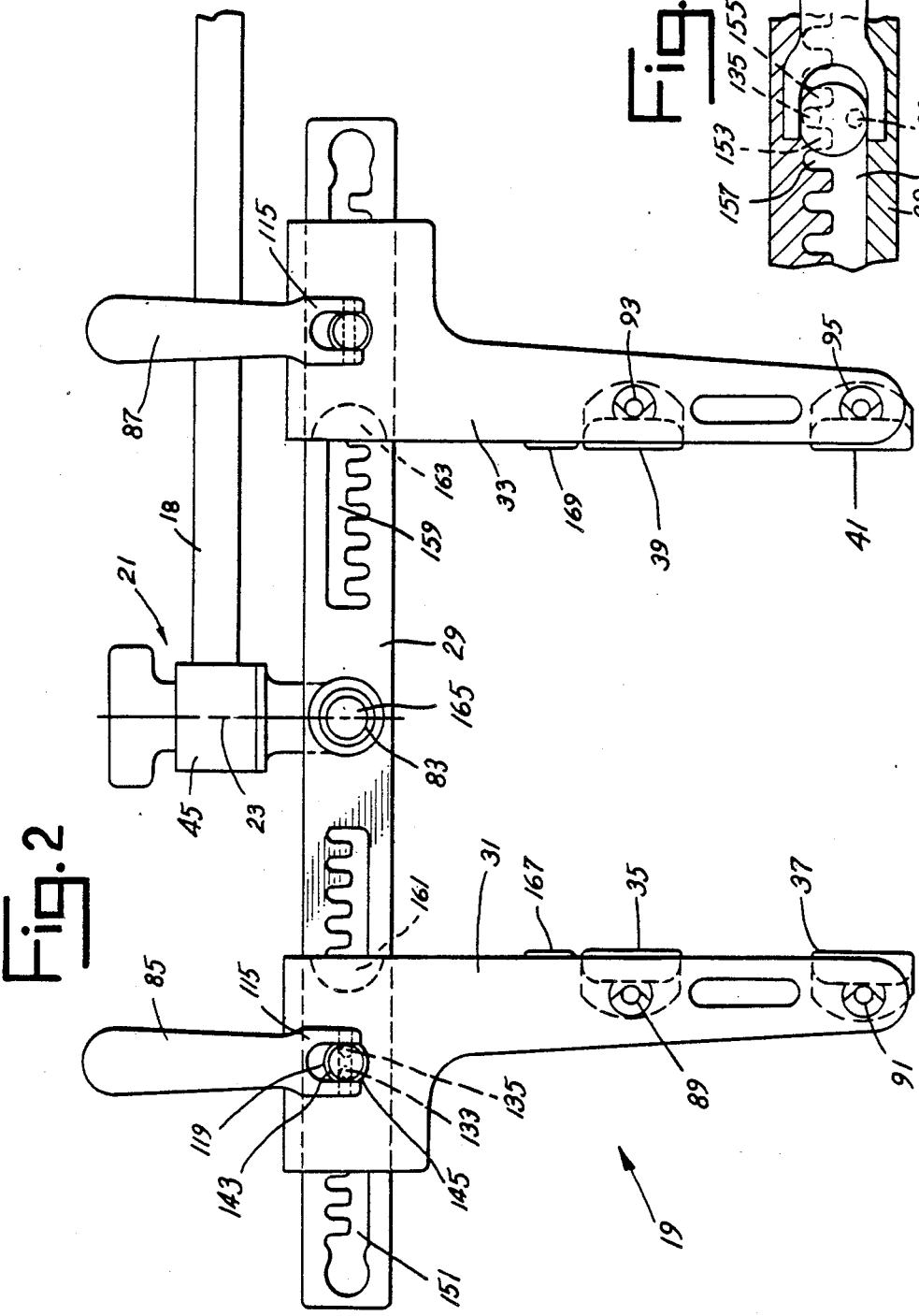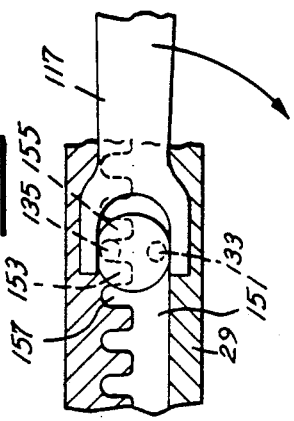

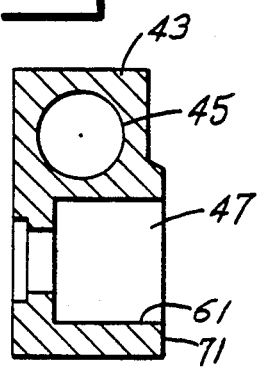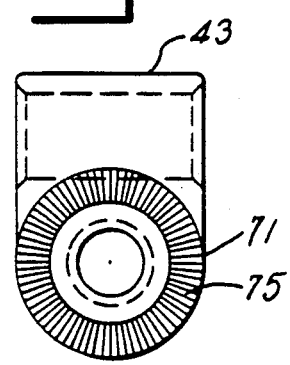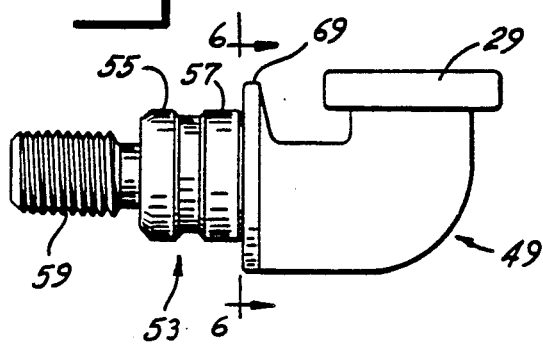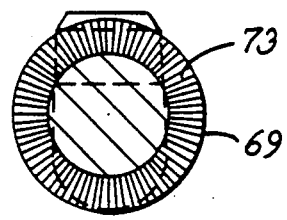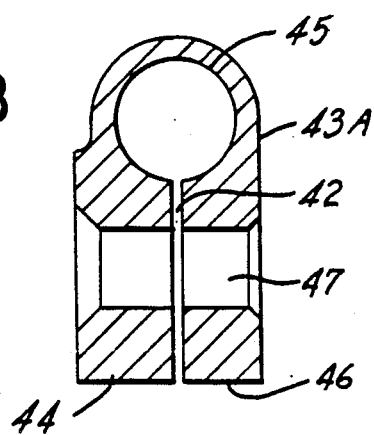

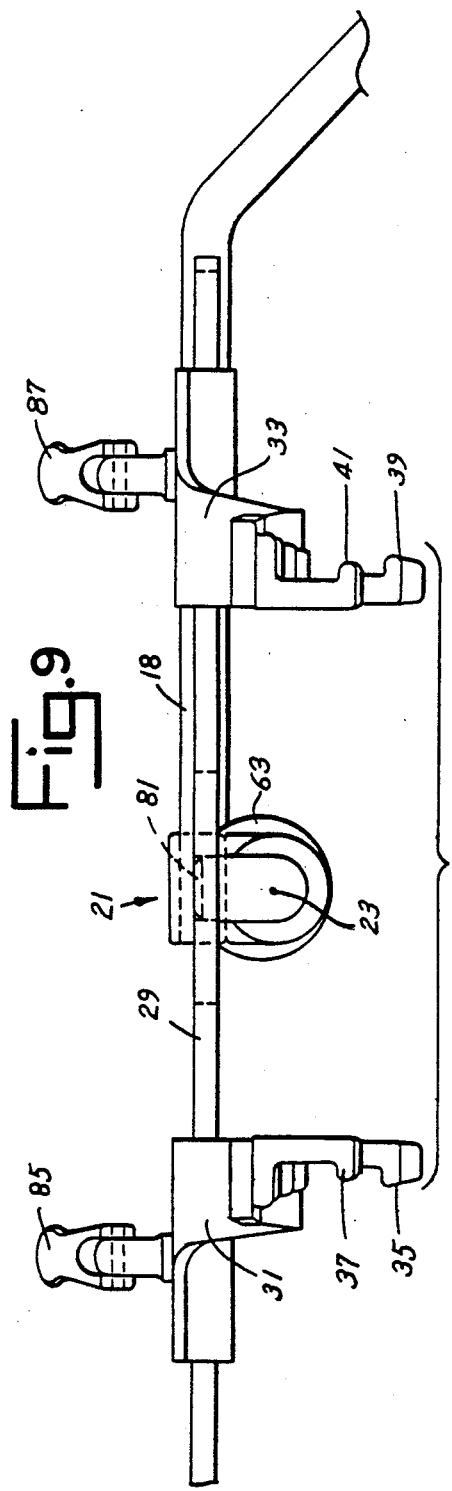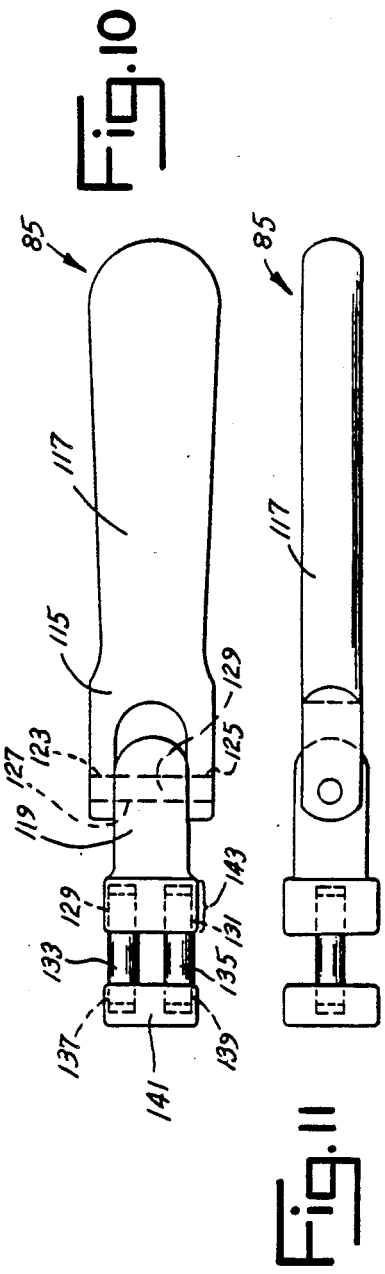

4,989,587

STERNAL RETRACTOR

BACKGROUND OF THE INVENTION

The invention relates to surgical apparatus for retracting the sternum and more particularly relates to retraction apparatus which exposes the Internal Mammary Artery (IMA) during coronary bypass surgery.

In surgical operations involving the chest cavity, a retraction apparatus is needed to retract bone structures to provide exposure to the operative site. Coronary bypass procedures necessitate retraction apparatus for exposing the Internal Mammary Artery which runs along the underside of the rib cage. The retraction apparatus must elevate one side of the rib cage while avoiding the application of downward pressure on the other side. Pressure applied to the sternum during surgery can cause trauma.

Heretofore, retraction devices performing sternal separation were tilted to expose the IMA, but such structure applied downward pressure on the non-elevated side of the rib cage. As mentioned above, such pressure can cause trauma in the patient.

To overcome the problem of downward pressure, retraction devices have been developed such as that disclosed in U.S. Pat. No. 3,572,326. However, such devices comprise a large number of components which make its assembly very difficult and time consuming. In many cases, such devices obstruct exposure of the IMA rather than facilitating it.

In order to simplify the set-up procedure, a table mounted retractor has been developed which comprises few components. However, such devices do not perform sternal spreading and thus the use of a separate sternal spreader to expose the heart for bypass preparation is required. The presence of a second device introduces a higher probability of non-sterility in the operating environment. Moreover, in operations requiring bilateral exposure of both IMAs, such retractors must be moved from one side of the surgical table to the other. Because the rail clamp which secures the retractor to the surgical table rail is disposed below the field of sterilization, any re-locating of the device presents sterility problems. In addition, moving the retractor wastes valuable time during surgery.

It is therefore an object of the present invention to provide an improved IMA retractor.

It is another object of the invention to provide a table mounted sternal retractor which eliminates downward pressure on the patient and facilitates quick and easy set-up.

It is a further object of the invention to provide a sternal retractor which reduces the possibility of contamination by eliminating relocation of the apparatus during bypass operations requiring bilateral exposure of the IMAs.

SUMMARY OF THE INVENTION

These and other objects of the invention are achieved in a sternal retraction device which includes a pivotal mechanism capable of elevating the rib cage to provide access to the IMA without applying downward pressure on the patient.

In addition, the device can include retraction arms which are positionable independently of one another giving the operator the ability to offset sternal spreading.

The device further includes a multi-directional connection joint adjustably linking a support post to an extension arm which supports the pivotal mechanism above the sternum of a patient lying on a conventional surgical table. In one embodiment, the device includes a rail clamp which can be adjusted in order to fasten the support post of the overall system anywhere along the rail of a conventional surgical table. The rail clamp can be positioned and adjusted from above the field of sterility thus facilitating a sterile operating environment.

BRIEF DESCRIPTION OF THE DRAWINGS

FIG. 1 is a perspective view of an overall sternal retraction system embodiment of the present invention.

FIG. 2 is a top view of the retraction system of FIG. 1.

FIG. 4 is a cross-sectional side view of a first embodiment of a brace block of the retraction system of FIG. 1.

FIG. 5 is a side view of a support brace of the retraction system of FIG. 1.

FIG. 6 is an end view along lines 6—6 of the support brace of FIG. 5.

FIG. 7 is an end view of the brace block of FIG. 4.

FIG. 8 is a cross-sectional side view of a second embodiment of a brace block of the retraction system of FIG. 1.

FIG. 9 is a front view of the pivot joint and retractor apparatus of FIG. 1.

FIGS. 10 and 11 are top and side views of the handles of FIG. 2.

FIG. 12 is a cross-sectional top view of a portion of the alignment bar and the securing handle mechanism of the retraction system of FIG. 1.

FIG. 13 is a top view of the retractor alignment bar of FIG. 2.

DETAILED DESCRIPTION OF A PREFERRED EMBODIMENT

Figure 3:
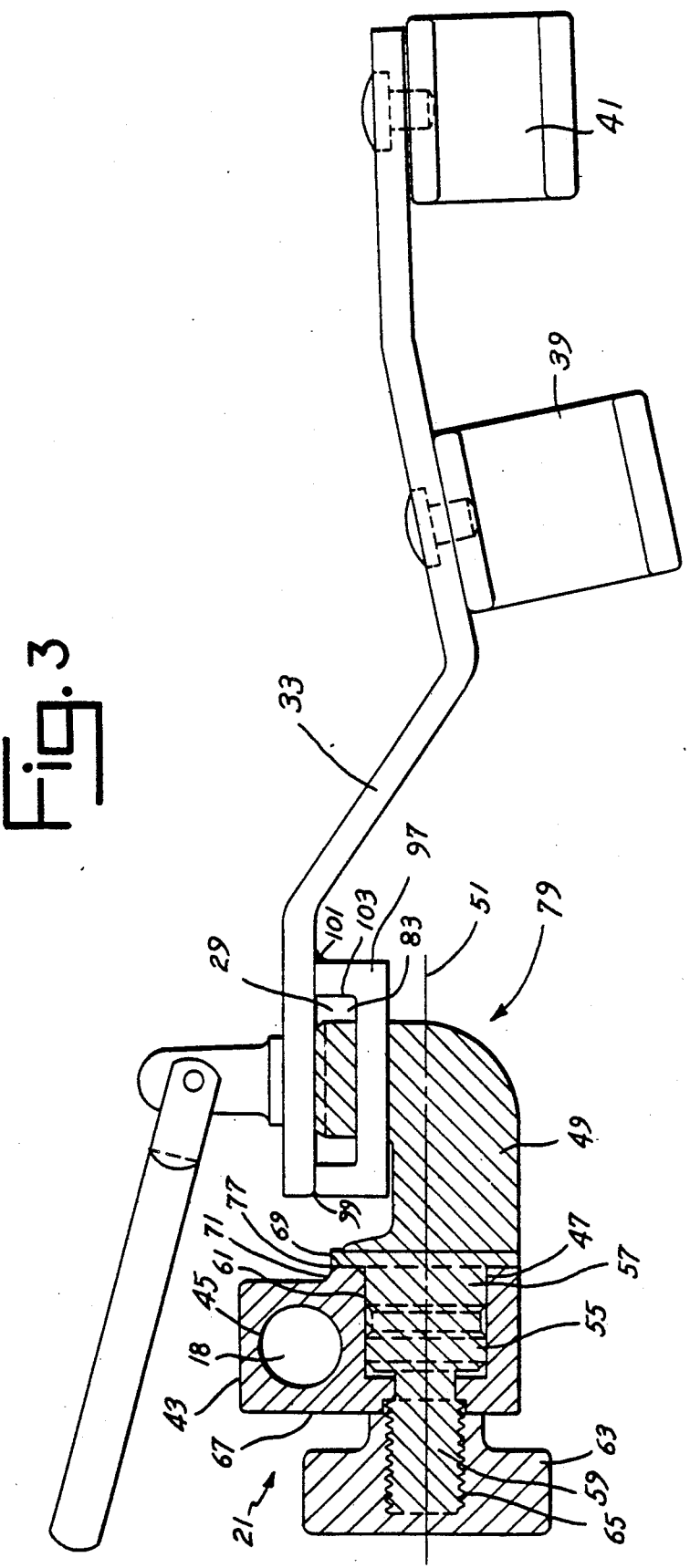
FIG. 3 is a cross-sectional side view of the retraction system of FIG. 1.

Referring to FIG. 1, a surgical sternal retraction system 11 includes a conventional rail clamp 13 (shown in block diagram form) which is securable to a rail 15 of a conventional operating table (not shown). A support post 17 extends vertically upward from rail clamp 13 slightly curving in the direction of the table at its upper end. A multi-directional connection joint 16 adjustably fastens an angled extension arm 18 to support post 17. Extension arm 18 supports a retractor apparatus 19 which is secured to extension arm 18 by a rotatable joint 21.

The multi-directional connection joint 16 in cooperation with the extension arm permits an operator to remotely position the retractor apparatus without breaking the field of sterilization. As will suggest itself, a rail clamp which is adjustable from above the field of sterilization may be used to fasten the retraction system to the surgical table rail. An adjustable rail clamp and multi-directional connection joint of the type mentioned above are disclosed in U.S. application Ser. No. 07/343,807 filed on even date herewith.

As shown in FIG. 2, rotatable joint 21 allows rotation of the retractor apparatus about an axis 23. Retractor apparatus 19 includes a retractor alignment bar 29, a pair of retraction arms 31, 33 and four retractor blades 35, 37, 39, 41. The retractor blades extend downwardly from the retraction arms, as shown in FIG. 3, for insertion within the sternum (not shown). As understood, the blades are used to spread and elevate bone structure thereby providing access to the operative site.

As shown in FIG. 3, rotatable joint 21 includes a brace block 43 having a passage or aperture 45 through which extension arm 18 passes. Extension arm 18 is permanently fixed within aperture 45 by a weld (not shown) or by other means.

As shown in FIG. 4, brace block 43 includes a second passage 47 which extends fully through the brace block. Passage 47 rotatably mounts a support brace 49 (FIG. 3) to permit its rotation about an axis 51. As shown in FIG. 5, support brace 49 includes a shaft portion 53 having a pair of cylindrical bearing surfaces 55, 57 and includes a threaded rod portion 59. As shown in FIG. 3, shaft portion 53 is housed within one portion of cavity 47 and bearing surfaces 55, 57 travel along the cylindrical wall surface 61 (FIG. 4) which defines the one portion of passage 47. Threaded rod portion 59 extends partially outside of passage 47 of the brace block having its threads disposed outside of the brace block as well as partially within a second portion of passage 47.

Referring again to FIG. 3, a knob 63 includes a threaded bore 65 which threadably receives threaded rod 59. As knob 63 is rotated in a clockwise direction, its threaded bore 65 engages threaded rod 59 and pulls the knob toward brace block 43 seating the knob against the backside 67 of brace block 43. Further rotation of knob 63 will pull support brace 49 against the front side or outcrop 71 of brace block 43. A front face or flange 69 of support brace 49 firmly seats against outcrop 71 as knob 63 is tightened.

As shown in FIGS. 6 and 7 both flange 69 (FIG. 6) and outcrop 71 (FIG. 7) have respective serrated surfaces 73, 75. Surfaces 73, 75 interlock at a juncture 77 (FIG. 3) to prevent rotational movement of support brace 49 relative to brace block 43 after knob 63 is tightened firmly.

As shown in FIG. 8, another embodiment of a brace block 43A is shown in which a slot or channel 42 passes through passage 47 in a plane orthogonal to passage 47 and extends into one side of passage 45. Channel 42 bifurcates brace block 43A into two sections, 44, 46. Extension arm 18 passes through passage 45 but extension arm 18 is not welded within the passage. Instead, as knob 63 is tightened, sections 44, 46 are drawn together in order to constrict the circumference of passage 45 about extension arm 18. This serves to tighten the brace block 43A onto extension arm 18 to fix the brace block thereto.

Support brace 49 is formed with an extension elbow 79 which curves upwardly presenting a support end 81, as shown in FIG. 9. Support end 81 serves to support retractor alignment bar 29. An aperture 83 (FIG. 3) is disposed at the midpoint of retractor alignment bar 29 and receives support end 81. A weld (not shown) permanently fastens support end 81 within the aperture 83.

Referring to FIG. 2, retraction arms 31, 33 are independently positionable along retractor alignment bar 29. The location of each retractor arm 31, 33 is adjusted by rotating respective cranks 85, 87. Each retraction arm 31, 33 carries a pair of retractor blades 35, 37 and 39, 41 which are mounted in a fixed position on arms 31, 33 by respective pairs of bolts 89, 91 and 93, 95 (FIG. 2). As shown in FIG. 9, blades 35–41 are U-shaped in configuration.

Referring again to FIG. 3, retraction arm 33 has one end which is mounted to retractor alignment bar 29 by means of a U-shaped bracket 97. Bracket 97 encompasses the lower and side portions of the alignment bar in closely spaced relation and is attached by welds 99, 101 to the underside of retraction arm 33. The passage 103 defined by retraction arm 33 and bracket 97 receives bar 29 permitting arm 33 to freely slide along the retractor alignment bar. As will suggest itself, retraction arm 31 is similarly mounted to retractor alignment bar 29.

As shown in FIGS. 2, 10 and 11, each manually operable crank 85, 87 includes a two-pronged fork 115 disposed at the end of a handle 117 and which encompasses a pivot post 119. Apertures 123, 125 formed in fork 115 and an aperture 127 formed in pivot post 119 are aligned to receive a dowel pin 129 which rotatably fastens handle 117 to pivot post 119.

A pair of positioning studs 133, 135 are disposed between pivot post 119 and a pivot plate 141. A pair of bored cylindrical cavities 129, 131 in the base 143 of the pivot post receive one end of studs 133, 135. The other end of the studs are received in a pair of cylindrical cavities 137, 139 formed in pivot plate 141.

Referring to FIGS. 2 and 12, base 143 of the pivot post rotates within an aperture 145 which is formed in the portion of the retractor arm lying directly over retractor alignment bar 29. Positioning studs 133, 135 extend through a toothed lock channel 151 of retractor alignment bar 29 and end below the toothed channel into pivot plate 141. Plate 141 is rotatably moveable within a bore (not shown) located in the lower portion of u-shaped bracket 97 (FIG. 3).

Referring to FIG. 12, as handle 117 of crank 85 is rotated in a clockwise direction, position studs 133, 135 alternately act as lever points thereby causing movement away from the center of alignment bar 29. When handle 117 is turned, position stud 135 which is wedged between teeth 153, 155 acts as a lever point causing position stud 133 to rotate past tooth 153 and into groove 157. Thereafter, position stud 133 becomes the new lever point as handle 117 continues its clockwise movement.

The operator locks retraction arm 31 in a desired position along alignment bar 29 by placing handle 117 in the position depicted in FIG. 12. In order to move retraction arm 31 back towards the center of the retractor alignment bar, the operator rotates crank handle 117 in a counter-clockwise direction.

As will suggest itself, retraction arm 33 can be variably positioned along the retractor alignment bar by rotating crank 87 in a manner similar to crank 85 as described above. A toothed lock channel 159 is similar to toothed lock channel 151 with the exception that its teeth are disposed on the opposite side of the channel thereby causing retraction arm 33 to move away from the center of retractor alignment bar 29 as crank 87 is rotated in a clockwise direction. Counter-clockwise rotation of crank 87 will move retraction arm 33 back towards the center of alignment bar 29.

The two separate lock channels 151, 159 disposed on opposing sides of retractor alignment bar 29 facilitate independent movement and placement of retraction arms 31, 33 as corresponding cranks 85, 87 are rotated and locked. A second embodiment of alignment bar 29 is shown in FIG. 13. As understood, independent placement of the retraction arms provides offset separation of the sternum.

As shown in FIG. 2, semi-circular cavities 161, 163 in retraction arms 31, 33 respectively are disposed in a position over retractor alignment bar 29 thereby allowing edges 167, 169 of retraction arms 31, 33 to come into contact despite a spot weld cap 165 atop aperture 83 of the alignment bar.

FIG. 9 provides greater detail of the upper portion of the retractor system. In operations necessitating exposure of the IMA (internal mammary artery), the operator of the system rotates cranks 85, 87 in a counterclockwise direction so as to bring together retraction arms 31, 33 along the retractor alignment bar. Retractor blades 35, 37 are placed against one side of the sternal incision while retractor blades 39, 41 are placed against the other. At this point, the operator rotates cranks 85, 87 in a clockwise direction causing retractor arms 31, 33 to horizontally spread the sternum thereby exposing the heart for bypass preparation. As previously mentioned, retraction arms 31, 33 can be positioned independent of one another thus allowing offset separation of the sternum.

After prepping the heart, the operator loosens knob 63, rotates retractor alignment bar 29 about pivot axis 23 to the desired angle, tightens knob 63 and using crank 85 or 87, elevates the retraction arm corresponding to the side of the rib cage under which the IMA is located thus providing IMA exposure. The elevated side of the rib cage wanting to return to its natural position exerts downward pressure on the raised side of retractor alignment bar 29. This downward pressure is transferred from the alignment bar to support post 17 via extension arm 18 and connection joint 21. Because support post 17 is attached directly to the surgical table, downward pressure is not exerted upon the patient thereby reducing the possibility of pressure induced trauma.

In operations involving bilateral exposure of the IMA's, the rotational characteristic of connection joint 21 enables the surgeon to rotate alignment bar 29 to alternately lift each side of the rib cage thereby exposing the IMA on the respective elevated side.

Following the harvesting of the exposed IMA, retractor apparatus 19 is again returned to a horizontal position by adjusting connection joint 21. After the bypass procedure requiring access to the heart has been executed, cranks 85, 87 are rotated in a counter-clockwise direction causing retractor arms 31, 33 to move toward each other along retractor bar 29. As the retraction arms are brought together, the rib cage contracts to its natural position. Retractor blades 35, 37, 39 and 41 are removed from the sternum completing the task of the retractor system 11.

While only a single, preferred embodiment of the invention has been described hereinabove, those of ordinary skill in the art will recognize that the embodiment may be modified and altered without departing from the central spirit and scope of the invention. Thus, the preferred embodiment described hereinabove is to be considered in all respects as illustrative and not restrictive, the scope of the invention being indicated by the appended claims, rather than by the foregoing description, and all changes which come within the meaning and range of equivalency of the claims are intended to be embraced herein.

What is claimed is:

1. A sternal retraction system for spreading and elevating a sternum during surgery to provide access to organs lying under said sternum, comprising:
    a support means mountable to a conventional surgical table;
    pivot joint means connected to said support means for providing an axis of rotation in a plane above the plane of the surgical table;
    alignment bar means secured to said pivot joint means for bidirectionally pivoting about said axis;
    retraction means including at least two retraction arms slidingly disposed on said alignment bar means for spreading said sternum, said retraction means including crank adjustment means manually crankable for independent positioning of one of said arms relative to the other of said arms, said crank adjustment means moving said one arm along the longitudinal axes of said alignment bar means as the adjustment means is cranked, said retraction means elevating a first side of said sternum upon the pivoting of said alignment bar means in a first rotational direction about said axis while permitting displacement of a said retraction arm by manual cranking of said adjustment means, said retraction means alternately elevating a second side of said sternum upon the pivoting of said alignment bar means in a second rotational direction about said axis while permitting displacement of a said retraction arm by manual cranking of said adjustment means.

2. A sternal retraction system according to claim 1 wherein said pivot joint means includes:
    (1) brace block means; and
    (2) support brace means rotatably mounted to said brace block means for rotation about said axis.

3. A sternal retraction system according to claim 2 wherein said pivot joint means includes securing means for preventing rotational movement between said support brace means and said brace block means.

4. A sternal retraction system according to claim 1 wherein said support means includes a rail clamp adjustably fastenable to the rail of a surgical table.

5. A sternal retraction system according to claim 1 wherein said retraction means includes at least one retractor blade, said blade supported by one of said retraction arms.

6. A sternal retraction system according to claim 1 wherein said alignment bar means includes a guide bar comprising toothed channel means enabling movement of said retraction means with respect to said alignment bar means.

7. A sternal retraction system according to claim 1 wherein said adjustment means includes a pair of manually operable cranks cooperating with said alignment bar means for positioning said retraction arms along said alignment bar means.

8. A sternal retraction system according to claim 3 wherein said securing means includes a first serrated surface formed on said support brace means adjacent to said brace block means.

9. A sternal retraction system according to claim 8 wherein said securing means further includes a second serrated surface disposed on said brace block means and adjacent to said first serrated surface, said second serrated surface cooperating with said first serrated surface to prevent rotational movement between said support brace means and said brace block means.

10. A sternal retraction system according to claim 9 wherein said securing means further includes a rotatable knob for controlling contact between said first and second serrated surfaces.

11. A sternal retractor system according to claim 1 wherein said crank adjustment means includes a pair of manually rotatable cranks each of said cranks cooperating with said alignment bar means for moving a respective one of said arms along said alignment bar means as its respective crank is rotated.

12. A sternal retraction system according to claim 11 wherein said alignment bar means includes first means for cooperating with said crank adjustment means for controlling movement of said arms.

13. A sternal retraction system according to claim 12 wherein said first means includes tooth channel means.

14. A sternal retraction system according to claim 13 wherein said adjustment means includes camming means moveable by said cranks and interacting with said tooth channel means.

* * * * *